US011206138B2

(12) United States Patent
Canterbury et al.

(10) Patent No.: US 11,206,138 B2
(45) Date of Patent: Dec. 21, 2021

(54) BIOSIGNATURE-BASED TOKENIZATION OF ASSETS IN A BLOCKCHAIN

(71) Applicants: Ernst & Young U.S. LLP, New York, NY (US); Ernst & Young Services (UK) Limited, London (GB)

(72) Inventors: James C. Canterbury, Hillsborough, NJ (US); Shyam Bharat Khatau, Chicago, IL (US); Parvez Hakim, Ilford (GB)

(73) Assignees: Ernst & Young U.S. LLP, New York, NY (US); EYGS LLP, London (GB)

( * ) Notice: Subject to any disclaimer, the term of this patent is extended or adjusted under 35 U.S.C. 154(b) by 246 days.

(21) Appl. No.: 16/654,720

(22) Filed: Oct. 16, 2019

(65) Prior Publication Data

US 2020/0351094 A1    Nov. 5, 2020

Related U.S. Application Data

(60) Provisional application No. 62/841,874, filed on May 2, 2019.

(51) Int. Cl.
*H04L 29/06* (2006.01)
*H04L 9/32* (2006.01)
(Continued)

(52) U.S. Cl.
CPC .......... *H04L 9/3213* (2013.01); *G06F 21/602* (2013.01); *G16H 10/40* (2018.01); *H04L 9/0637* (2013.01); *H04L 2209/38* (2013.01)

(58) Field of Classification Search
CPC . H04L 9/3213; H04L 9/0637; H04L 2209/38; G16H 10/40; G06F 21/602
(Continued)

(56) References Cited

U.S. PATENT DOCUMENTS 5,892,900 A    4/1999  Ginter et al.
9,397,985 B1   7/2016  Seger, II et al.
(Continued)

FOREIGN PATENT DOCUMENTS

CN    107274184 A    10/2017
CN    110033377 A    7/2019
(Continued)

OTHER PUBLICATIONS

European Commission, "Code of Conduct on Withholding Tax," [Online], Ref. Ares(2017)5654449—Nov. 20, 2017, Retrieved from the Internet: https://ec.europa.eu/taxation_customs/sites/taxation/files/code_of_conduct_on_witholding_tax.pdf, 12 pages.
(Continued)

*Primary Examiner* — Evans Desrosiers
(74) *Attorney, Agent, or Firm* — Cooley LLP

(57) ABSTRACT

An apparatus includes a tester to detect a biological signature of a biological sample, a processor, and a memory operably coupled to the processor. The memory stores instructions to cause the processor to receive an indication of the biological signature from the tester, and to generate, using a smart contract and through communication with a distributed ledger, a cryptographic token including a digital identifier based on the biological signature. The cryptographic token is transmitted to a remote processor for verification of the biological sample, in response to receiving the cryptographic token. The tester can detect the biological signature within a predetermined test duration that is less than a DNA sequencing duration associated with the biological sample, and the biological signature has a data precision sufficient to uniquely identify the biological sample from a plurality of biological samples.

18 Claims, 4 Drawing Sheets

(51) Int. Cl.
   G16H 10/40       (2018.01)
   G06F 21/60       (2013.01)
   H04L 9/06        (2006.01)

(58) Field of Classification Search
   USPC .......................................................... 713/159
   See application file for complete search history.

(56) References Cited

U.S. PATENT DOCUMENTS

| | | |
|---|---|---|
| 9,608,829 B2 | 3/2017 | Spanos et al. |
| 9,785,369 B1 | 10/2017 | Ateniese et al. |
| 9,794,074 B2 | 10/2017 | Toll et al. |
| 9,870,508 B1 | 1/2018 | Hodgson et al. |
| 9,881,176 B2 | 1/2018 | Goldfarb et al. |
| 9,906,513 B1 | 2/2018 | Wuehler |
| 9,942,231 B1 | 4/2018 | Laucius et al. |
| 9,948,467 B2 | 4/2018 | King |
| 9,959,065 B2 | 5/2018 | Ateniese et al. |
| 10,026,118 B2 | 7/2018 | Castinado et al. |
| 10,298,395 B1 | 5/2019 | Schiatti et al. |
| 10,438,290 B1 | 10/2019 | Winklevoss et al. |
| 10,540,654 B1 | 1/2020 | James et al. |
| 10,721,069 B2 | 7/2020 | Konda et al. |
| 2009/0204517 A1 | 8/2009 | Edens et al. |
| 2012/0108446 A1* | 5/2012 | Wu ........................ C12Q 1/6886 506/7 |
| 2014/0109245 A1* | 4/2014 | Pestell .................... A61P 35/00 800/10 |
| 2015/0018406 A1* | 1/2015 | Glimcher ............... A61K 45/06 514/44 A |
| 2016/0260169 A1 | 9/2016 | Arnold et al. |
| 2016/0358165 A1 | 12/2016 | Maxwell |
| 2017/0091750 A1 | 3/2017 | Maim |
| 2017/0278100 A1 | 9/2017 | Kraemer et al. |
| 2017/0293503 A1 | 10/2017 | Curtis |
| 2017/0316162 A1 | 11/2017 | Wall Warner et al. |
| 2017/0346639 A1 | 11/2017 | Muftic |
| 2018/0048461 A1 | 2/2018 | Jutla et al. |
| 2018/0082043 A1 | 3/2018 | Witchey et al. |
| 2018/0101701 A1 | 4/2018 | Barinov et al. |
| 2018/0139043 A1 | 5/2018 | Jayachandran et al. |
| 2018/0165131 A1 | 6/2018 | O'Hare et al. |
| 2018/0189753 A1 | 7/2018 | Konda et al. |
| 2018/0218176 A1 | 8/2018 | Voorhees et al. |
| 2018/0218469 A1 | 8/2018 | Lert, Jr. et al. |
| 2018/0237863 A1* | 8/2018 | Namsaraev ............ G16B 40/20 |
| 2019/0007381 A1 | 1/2019 | Isaacson et al. |
| 2019/0012662 A1 | 1/2019 | Krellenstein et al. |
| 2019/0034923 A1 | 1/2019 | Greco et al. |
| 2019/0080407 A1 | 3/2019 | Molinari et al. |
| 2019/0130701 A1 | 5/2019 | Simons |
| 2019/0164153 A1 | 5/2019 | Agrawal et al. |
| 2019/0164223 A1 | 5/2019 | De Jong |
| 2019/0279204 A1 | 9/2019 | Norton et al. |
| 2019/0299105 A1 | 10/2019 | Knight |
| 2019/0385156 A1 | 12/2019 | Liu |
| 2020/0034834 A1 | 1/2020 | Li et al. |
| 2020/0059361 A1 | 2/2020 | Konda et al. |
| 2020/0059362 A1 | 2/2020 | Brody et al. |
| 2020/0059364 A1 | 2/2020 | Konda et al. |
| 2020/0322154 A1 | 10/2020 | Konda et al. |
| 2020/0327473 A1 | 10/2020 | Zur et al. |
| 2020/0328893 A1 | 10/2020 | Westland |
| 2020/0351093 A1 | 11/2020 | Madhuram et al. |
| 2021/0042746 A1 | 2/2021 | Westland |
| 2021/0150626 A1 | 5/2021 | Robotham |

FOREIGN PATENT DOCUMENTS

| | | |
|---|---|---|
| WO | WO 2017/187395 | 11/2017 |
| WO | WO 2017/198891 | 11/2017 |
| WO | WO 2018/007828 | 1/2018 |
| WO | WO 2018/028777 | 2/2018 |
| WO | WO 2018/144302 | 8/2018 |
| WO | WO 2018/150275 | 8/2018 |
| WO | WO 2018/163044 | 9/2018 |
| WO | WO 2018/209153 | 11/2018 |

OTHER PUBLICATIONS

European Commission, "Non-paper on the withholding tax for discussion at the Expert Group on barriers to free movement of capital," Sep. 28, 2016, https://ec.europa.eu/transparency/regexpert/index.cfm?do=groupDetail.groupDetailDoc&id=28783&no=6 (last accessed Mar. 17, 2021), 6 pages.

European Parliament, Press Release, "Cum-ex tax fraud scandal: MEPs call for inquiry, justice, and stronger tax authorities," [Online], Nov. 29, 2018, Retrieved from the Internet: https://www.europarl.europa.eu/news/en/press-room/20181120IPR19552/cum-ex-tax-fraud-meps-call-for-inquiry-justice-and-stronger-tax-authorities, 4 pages.

European Parliament Resolution of Nov. 29, 2018 on the cum-ex scandal: financial crime and loopholes in the current legal framework (2018/2900(RSP), [Online], Retrieved from the Internet: http://www.europarl.europa.eu/doceo/document/TA-8-2018-0475_EN.html, May 19, 2020, 3 pages.

International Search Report and Written Opinion for International Application No. PCT/EP2020/072325, dtaed Nov. 6, 2020, 11 pages.

International Search Report and Written Opinion for International Application No. PCT/US2020/061243, dated Feb. 22, 2021, 12 pages.

International Search Report and Written Opinion for International Application No. PCT/US2021/027448, dated Jul. 23, 2021, 11 pages.

ISO 20022, "A single standardisation approach (methodology, process, repository) to be used by all financial standards initiatives," May 2013, [Online], Retrieved from the Internet: https://www.iso20022.org/, 6 pages.

ISO 6166—ISIN—International Securities Identification Number, [Online], Retrieved from the Internet: https://www.isin.net/iso-6166/, Retrieved from the Internet: May 2, 2021, 9 pages.

ISO 6166:2013, "Securities and related financial instruments International securities identification numbering system (ISIN)," Jul. 2013, [Online], Retrieved from the Internet: https://www.iso.org/standard/44811.html, 3 pages.

Kyle, L., "Overview of EY Nightfall," Jun. 13, 2019, [Online], Retrieved from the Internet: https://medium.com/coinmonks/overview-of-ey-nightfall-f9e9ce21cf65, 11 pages.

Lielacher, A., "Ernst & Young Rolls Out 'Nightfall' to enable private transactions on Ethereum," Brave New Coin, Jun. 7, 2019, [Online], Retrieved from the Internet: https://bravenewcoin.com/insights/ernst-and-young-rolls-out-'nightfall-to-enable-private-transactions-on, 6 pages.

OECD (2017), "Commentary on Article 10 Concerning The Taxation on Dividends," In Model Tax Convention on Income and on Capital: Condensed Version 2017, OECD Publishing, Paris, [Online], Retrieved from the Internet: https://read.oecd-ilibrary.org/taxation/model-tax-convention-on-income-and-on-capital-condensed-version-2017_mtc_cond-2017-en, pp. 231-253.

OECD (2020), Centre for Tax Policy and Administration, Glossary of Tax Terms, "Withholding Tax," [Online], Retrieved from the Internet: https://www.oecd.org/ctp/glossaryoftaxterms.htm, 23 pages.

OECD (2020), "TRACE XML Schema: User Guide," OECD, Paris [Online], Retrieved from the Internet: http://www.oecd.org/tax/exchange-of-tax-information/trace-XML-schema-user-guide.htm, 70 pages.

OECD, "Action 13 Country-by-Country Reporting," [Online], Retrieved from the Internet: https://www.oecd.org/tax/beps/beps-actions/action13/, 7 pages.

OECD, Common Reporting Standard (CRS)—Organisation for Economic Co-operation and Development, "What is the CRS?" Jul. 15, 2014, [Online], Retrieved from the Internet: https://www.oecd.org/tax/automatic-exchange/common-reporting-standard/, 3 pages.

(56) References Cited

OTHER PUBLICATIONS

OECD, "TRACE Implementation Package," Jan. 23, 2013, [Online], Retrieved from the Internet: https://www.oecd.org/ctp/exchange-of-tax-information/TRACE_Implementation_Package_Website.pdf, 135 pages.

Office Action for U.S. Appl. No. 16/869,944, dated Dec. 3, 2020, 24 pages.

Office Action for U.S. Appl. No. 16/869,944, dated May 21, 2021, 22 pages.

Office Action for U.S. Appl. No. 16/904,296, dated Jun. 10, 2021, 27 pages.

Office Action for U.S. Appl. No. 16/952,949, dated Jun. 15, 2021, 23 pages.

Planta, F., European Securities and Markets Authority (esma), European Parliament—FISC Sub Committee on Fiscal Matters, "Public hearing on Cum/Exand Cum/Cum scandal," Feb. 22, 2021, ESMA70-155-11890, Retrieved from the Internet: https://www.esma.europa.eu/sites/default/files/library/esma70-155-11890_statement_cumex_cumcum_scandal_-_fabrizio_planta.pdf, 3 pages.

Shahid, A. et al., "Blockchain-based agri-food supply chain: A complete solution," IEEE Access, IEEE, vol. 8, Apr. 2020, pp. 69230-69243.

Westerkamp, M. et al., "Blockchain-based supply chain traceability: Token recipes model manufacturing processes," 2018 IEEE Confs on Internet of Things, Green Computing and Communications, Cyber, Physical and Social Computing, Smart Data, Blockchain, Computer and Information Technology, Congress on Cybermatics, IEEE, Jul. 2018, pp. 1595-1602.

International Search Report and Written Opinion for International Application No. PCT/US2019/056646, dated Jan. 15, 2020, 12 pages.

Office Action for U.S. Appl. No. 16/283,452, dated Jul. 10, 2019, 31 pages.

Office Action for U.S. Appl. No. 16/283,452, dated Nov. 6, 2019, 34 pages.

International Search Report and Written Opinion for International Application No. PCT/US2019/046532, dated Dec. 2, 2019, 10 pages.

International Search Report and Written Opinion for International Application No. PCT/US2019/046808, dated Dec. 2, 2019, 9 pages.

International Search Report and Written Opinion for International Application No. PCT/US2019/057246, dated Feb. 4, 2020, 8 pages.

International Search Report and Written Opinion for International Application No. PCT/US2019/057262, dated Jan. 24, 2020, 9 pages.

International Search Report and Written Opinion for International Application No. PCT/EP2020/060588, dated Jun. 24, 2020, 13 pages.

International Search Report and Written Opinion for International Application No. PCT/US2020/028128, dated Jun. 25, 2020, 9 pages.

Andreev, O., "Hidden in Plain Sight: Transacting Privately on a Blockchain. Introducing Confidential Assets in the Chain Protocol," [Online], Retrieved from the Internet: <URL: https://blog.chain.com/hidden-in-plain-sight-transacting-privately-on-a-blockchain-835ab7 . . . ], Retrieved on Aug. 27, 2018, 11 pages.

Ben-Sasson, E. et al., "Scalable, transparent, and post-quantum secure computational integrity," Cryptology ePrint Archive, Report 2018/046 (2018), 83 pages.

International Telecommunication Union, Telecommunication Standardization Sector, Focus Group on Application of Distributed Ledger Technology, DLT-O-067, Output Document, "Updated baseline text: D4.1-DLT regulatory framework," Apr. 2019, 45 pages.

Lee, C. H. et al., "Implementation of IoT system using blockchain with authentication and data protection," 2018 International Conference on Information Networking (ICOIN), IEEE, Jan. 10, 2018, pp. 936-940.

Menezes, A. et al., "Key Management Techniques," Chapter 13 in Handbook of Applied Cryptography, CRC Press, Boca Raton, FL, (1996), pp. 543-590.

Narula, N. et al., "zkLedger: Privacy-preserving auditing for distributed ledgers," Proceedings of the 15th USENIX Symposium on Networked Systems Design and Implementation (NSDI '18), Apr. 9-11, 2018, Renton, WA, USA, 17 pages.

Parno, B. et al., "Pinocchio: Nearly practical verifiable computation," S&P (2013), 16 pages.

Groth, J. et al., "Snarky signatures: Minimal signatures of knowledge from simulation-extractable SNARKs," In: Katz, J., Shacham, H. (eds.) Crypto 2017. LNCS, vol. 10402, pp. 581-612. Springer, Cham (2017).

Wu, H., "DIZK: Distributed zero-knowledge proof systems," In USENIX Security (2018), 35 pages.

Orcutt, M., "A tool developed for blockchains makes it possible to carry out a digital transaction without revealing any more Information than absolutely necessary," MIT Technology Review 121.2: 45(1). Technology Review, Inc. (Mar. 2018-Apr. 2018).

Zhang, Y. et al., "Z-Channel: Scalable and efficient scheme in zerocash," 2017, [Online], Retrieved from the Internet: https://eprint.iacr.org/2017/684, pp. 1-39.

Wang, X. et al., "STAMP: Enabling Privacy-Preserving Location Proofs for Mobile Users," IEEE/ACM Transactions on Networking, vol. 24, No. 6, Dec. 2016, pp. 3276-3289.

Kosba, A. et al., "Hawk: The Blockchain Model of Cryptography and Privacy-Preserving Smart Contracts," 2016 IEEE Symposium on Security and Privacy, May 2016, pp. 839-858.

\* cited by examiner

BIOSIGNATURE-BASED TOKENIZATION OF ASSETS IN A BLOCKCHAIN

CROSS-REFERENCE TO RELATED APPLICATIONS

This application claims priority to and benefit of U.S. Provisional Application No. 62/841,874, titled "Biosignature-Based Tokenization of Assets in a Blockchain," filed May 2, 2019, the entire disclosure of which is incorporated herein by reference in its entirety.

TECHNICAL FIELD

The present disclosure generally relates to the biosignature-based tracking and validation of biological and other sensitive samples within a supply chain, using a distributed ledger.

BACKGROUND

Maintaining the integrity of a chain of custody for a biological sample has previously been accomplished using one or more tracking mechanisms, such as labels, RFID tags, etc., which are affixed to the packaging containing the biological sample.

SUMMARY

In some embodiments, an apparatus includes a tester configured to detect a biological signature (e.g., a disease-agnostic biological signature) of a biological sample (e.g., human blood, non-human mammalian blood, urine, hair, nail, saliva, food, tumor tissue, musculoskeletal tissue, etc.) or other specimen, a processor, and a memory operably coupled to the processor. The memory stores instructions to cause the processor to receive an indication of the biological signature from the tester, and to generate (e.g., via the processor), or to initiate generation of (e.g., via communication with a remote compute device), using a smart contract and through communication with a distributed ledger, a cryptographic token ("token") including a digital identifier based on the biological signature (and, optionally, at least one of a date, a time, a location, or patient information). The cryptographic token is transmitted to a remote processor configured to verify the biological sample in response to receiving the cryptographic token. The tester can be configured to detect the biological signature within a predetermined test duration that is less than a DNA sequencing duration associated with the biological sample, and the biological signature has a data precision sufficient to uniquely identify the biological sample from a plurality of biological samples.

In some embodiments, a method includes receiving a signal representing a first cryptographic token including a biological signature (or "biosignature") associated with a biological sample, and storing, in response to receiving the signal, a representation of the first cryptographic token and an identifier of the biological sample in a distributed ledger. A query is received, the query including the identifier of the biological sample, and in response to and based on the query, a signal representing the cryptographic token is transmitted. The biosignature (e.g., biological/blood/plasma analyte analysis biosignature, an image-based analysis biosignature, or a biomechanical analysis biosignature) can be generated using a test methodology, and each of a first sample verification and a second sample verification can be performed using the test methodology. The query can be a first query, received from a server associated with an intermediate testing facility. The transmitting the signal representing the cryptographic token can be to the server associated with an intermediate testing facility for the first sample verification. The method can also include receiving, from a server associated with a destination facility, a second query including the identifier of the biological sample, and transmitting, in response to and based on the second query, a signal representing the cryptographic token to the server associated with the destination facility for the second sample verification.

In some embodiments, a process includes receiving, from a patient and at a first site, a biological sample. A first test, is run at the first site, and a first unique identifier associated with the biological sample is generated based on the first test. A blockchain/cryptographic token is generated using the unique identifier, optionally in combination with a set of one or more attributes such as a patient identifier, date/time of biological sample receipt/production, etc. The biological sample is sent to a second site different from the first site. A second test, having a same test type/methodology as that of the first test, is performed at the second site on the biological sample, and a second unique identifier associated with the biological sample is generated based on the second test. The second unique identifier is combined with the set of one or more attributes, and a determination is made as to whether the second unique identifier (optionally in combination with the set of one or more attributes) matches the first unique identifier (optionally in combination with the set of one or more attributes). If the values do match, the biological sample may be deemed "verified" or "authentic."

DETAILED DESCRIPTION

Figure 1:
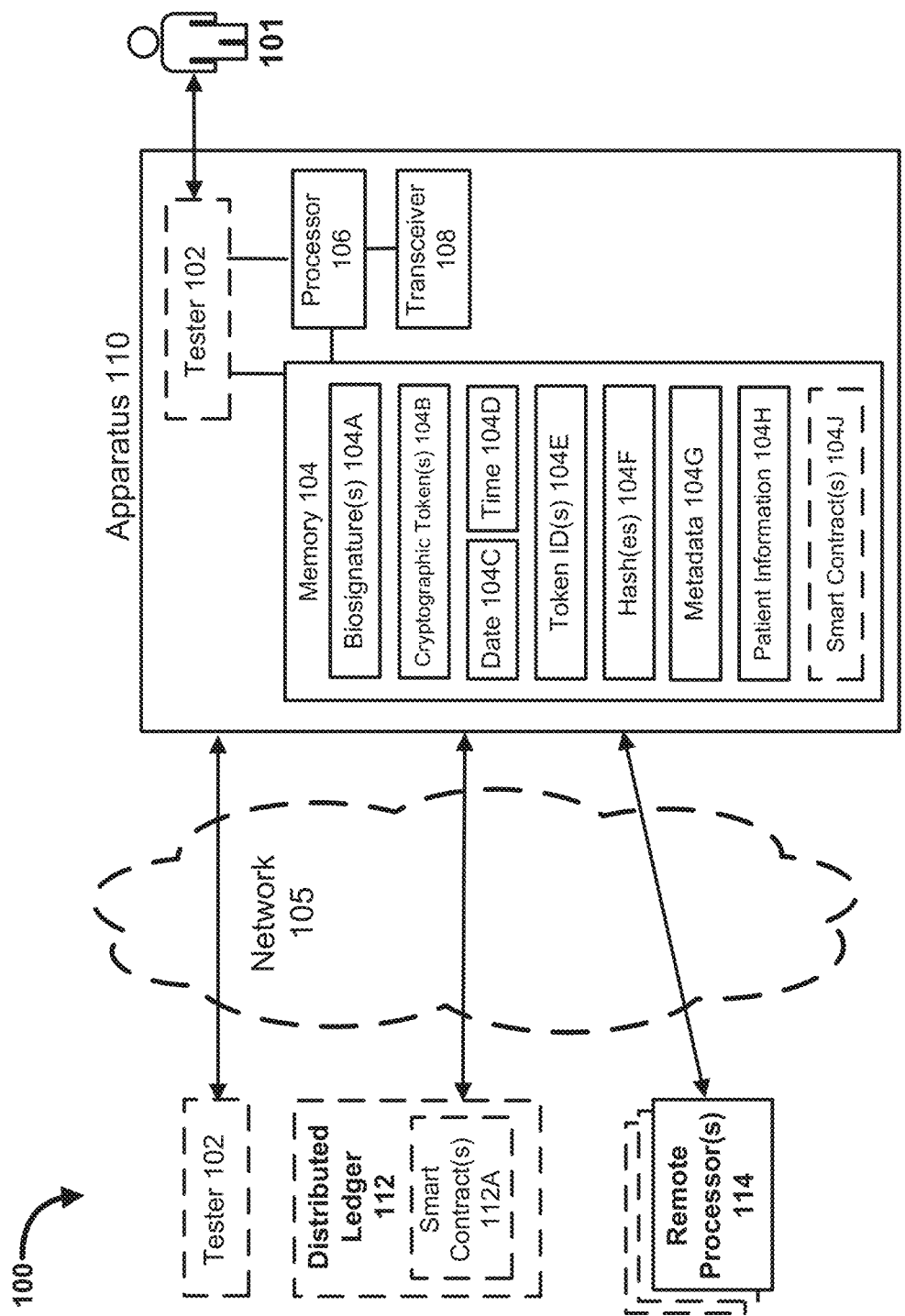
FIG. 1 is a system diagram illustrating a system for validation and tracking of a biological sample, according to some embodiments.

Maintaining the integrity of a chain of custody for a biological sample (or biological "asset") as it is transported or transferred within a supply chain has previously been accomplished using one or more tracking mechanisms, such as labels, RFID tags, etc., which are affixed to the physical packaging containing the biological sample. Such approaches are susceptible, however, to issues such as mislabeling of packages, destruction of the packaging, and degradation or erasure of the label. Moreover, the integrity of the chain of custody often depends on the coordination of several disparate systems, owned/managed by multiple different parties, for proper implementation and integration. This entity interdependence can result in reconciliation issues, a time lag in the availability of data, and/or other data integrity related concerns.

Methods of the present disclosure address the foregoing issues by linking an identifier of the biological sample to one or more characteristics of the biological sample itself. As such, using methods set forth herein, a biological sample can be traced to its source, even in the absence of a packaging label. A blockchain (or any distributed ledger) can be also be used to register and track the biological sample, thereby further alleviating concerns related to data integrity/availability and system integration cost. Methods of the present disclosure can be more effective than known tracking methods, in that they facilitate independent verification of the identity of the biological sample, are less susceptible to tampering (since tampering with the blockchain would involve collusion among multiple parties, as well as modification of tamper-resistant software/hardware), and provide a more reliable ("provable") audit trail of samples to regulators.

In some embodiments, a method for tracking and/or validation of a biological asset includes generating a unique representation of the biological asset as a non-fungible token within a blockchain by incorporating the results of a first biosignature scan, of or associated with that biological asset, into the definition of a unique token ID. In some such implementations, the method also includes the placement of one or more physical labels on the biological sample and/or its packaging (e.g., transport container), where the one or more physical labels also include the unique token ID. Once the token has been defined, a second biosignature scan (e.g., similar to the first biosignature scan, but at a different location within the supply chain) can subsequently be performed, and the results of the second biosignature scan can be compared with the token within the blockchain. In some embodiments, as the biological asset is transported, the associated token is transferred or modified within the blockchain such that the associated address within the blockchain represents or is associated with a physical location of the biological asset. As used herein, a "token" refers to a cryptographic token, defined as a representation of an asset or utility on a blockchain. A "biological token" refers to a cryptographic representation of a biological material, using one or more of the methods set forth herein.

Figure 2:
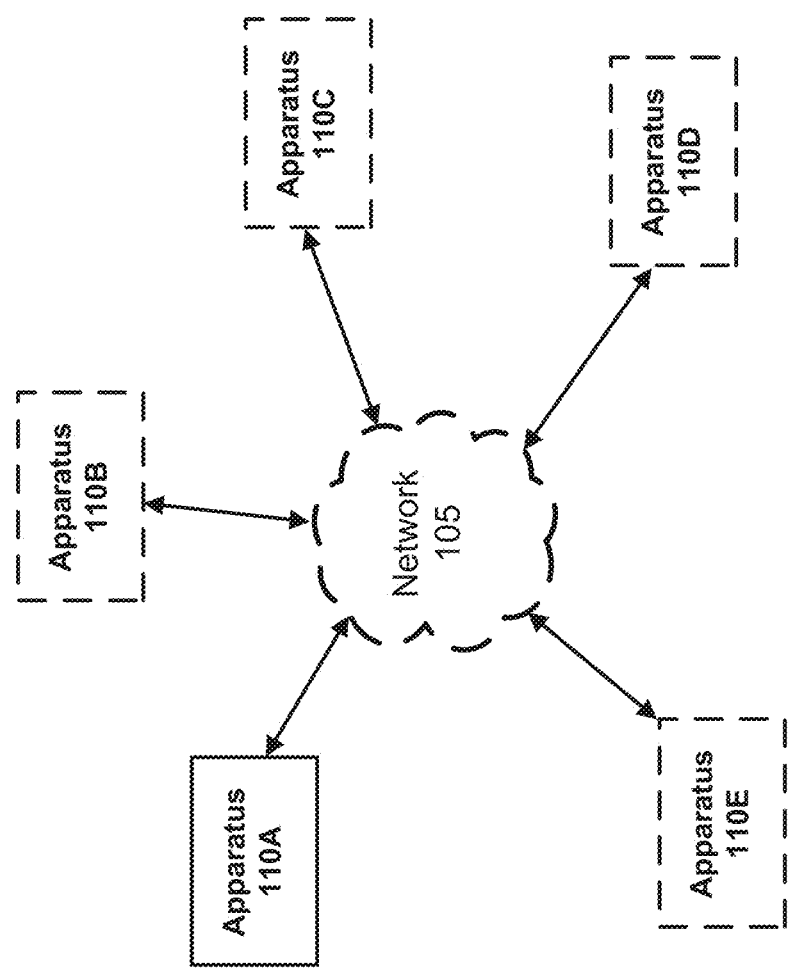
FIG. 2 is a system diagram illustrating a system for validation and tracking of a biological sample, including multiple apparatuses of FIG. 1.

FIG. 1 is a system diagram illustrating a system for validation and tracking of a biological sample, according to some embodiments. As shown in FIG. 1, a system 100 includes an apparatus 110, in communication (e.g., via a wireless network 105) with one or more remote processors 114 and, optionally, a distributed ledger 112 (e.g., a blockchain). The distributed ledger 112 can include, or can reference a representation of or reference to, one or more smart contracts (e.g., ERC-721, ERC-20, ERC-223, or ERC-777) 112A. The apparatus 110 can include an onboard tester 102 in operable communication with a processor 106. Alternatively, the apparatus may be in wired or wireless network communication with a tester that is physically separate from the apparatus. The tester 102 can be any instrument for analyzing a sample of biological material (e.g., tissue, fluids such as blood or urine, etc.) derived from a patient 101. One or both of the tester 102 and the processor 106 is communicatively coupled to a memory 104. The memory 104 stores one or more biosignatures (e.g., referred to herein as biosignature strings) 104A, cryptographic tokens 104B, date 104C and time 104D information (e.g., associated with the one or more biosignatures 104A), token IDs 104E, hashes 104F (e.g., associated with the one or more biosignatures 104A), metadata 104G, and/or patient information 104H. The memory 104 can optionally also store location information (e.g., associated with the biosignature scan), environmental data during shipping and/or storage (e.g., temperature, humidity, and/or light conditions), and/or transport data (e.g., via air or ground). The memory 104 also optionally stores one or more smart contracts 104J (or data associated therewith). In some implementations, each cryptographic token 104B from the cryptographic tokens 104B is generated by the processor 106 (e.g., according to instructions stored in the memory 104) and includes a hash 104F and an associated portion of the metadata 104G, as discussed in further detail below. In other implementations, the generation of the cryptographic token(s) is initiated by the processor when the processor sends a signal representing an instruction to generate the cryptographic token(s) to a remote compute device. In some implementations, a system can include multiple apparatuses 110, as shown in FIG. 2. Each of the multiple apparatuses 110A-110E in such a system can be in network communication with one another via a network 105.

As used herein, a "patient" can refer to, but is not limited to, an individual undergoing medical treatment. Other meanings of the term "patient" herein can include an athlete or any other individual subject to drug testing, an animal undergoing medical treatment, an animal (live or dead) intended for consumption, a consumer sending a biological sample (e.g., DNA) for genetic testing, an arrestee, inmate, or other individual associated with an arrest or criminal proceeding, etc.

Systems and methods described herein can be performed by software (stored in memory 104 and/or executed on hardware), hardware, or a combination thereof. Processor 106 can refer to one or more hardware modules, each of which can be any of, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code. Each of the devices described herein can include one or more processors (e.g., processor 106) as described above.

Figure 3:
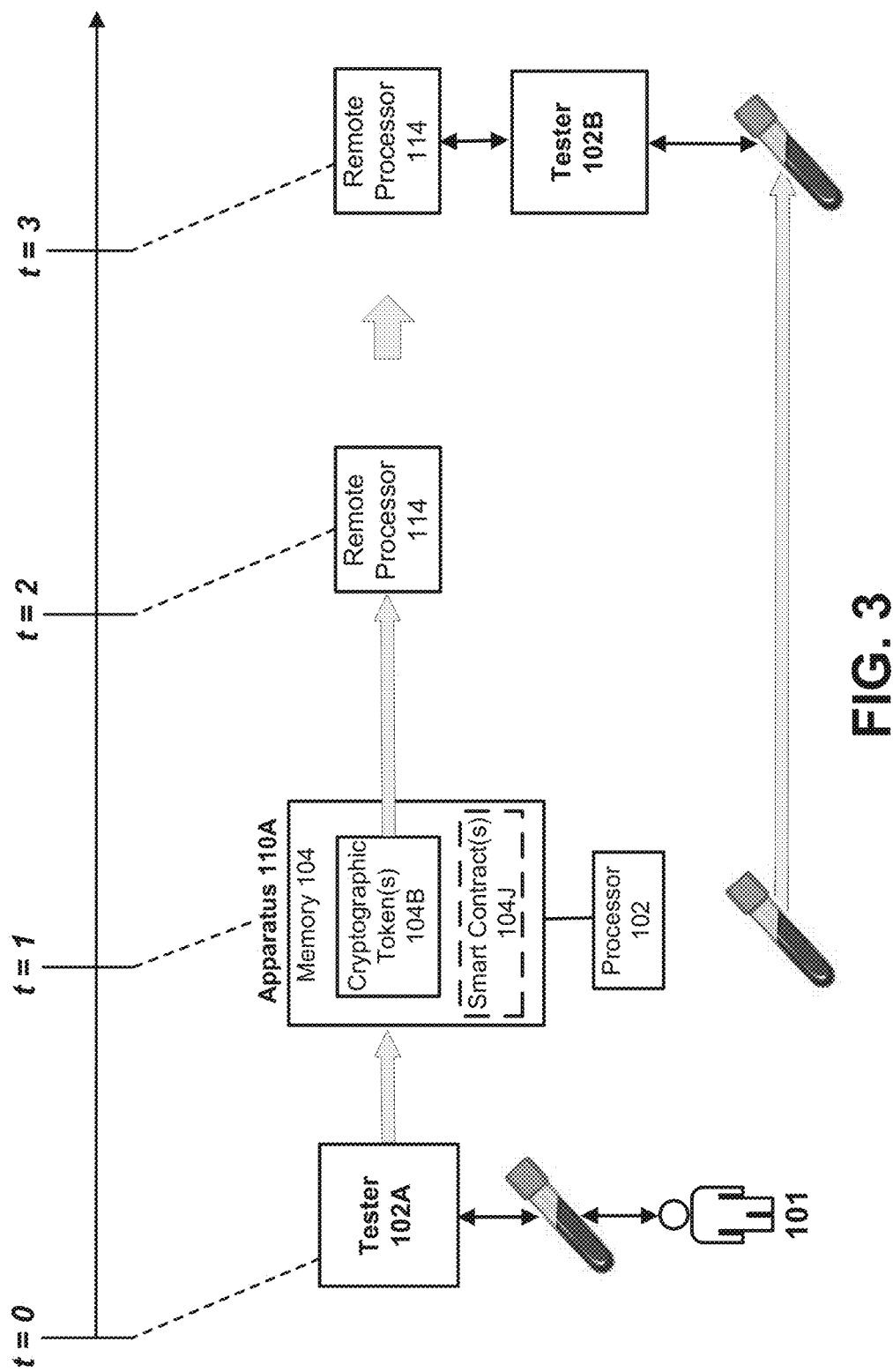
FIG. 3 is a flowchart illustrating an example sequence of events associated with a biological samples within a supply chain, using components of system 100 in FIG. 1, according to some embodiments.

FIG. 3 is a flowchart illustrating an example sequence of events associated with a biological samples within a supply chain, using components of system 100 in FIG. 1, according to some embodiments. As shown in FIG. 3, at an initial time (t=0), a biological sample derived from and/or provided by a patient 101 is tested using a first tester 102A at a first location. The test performed by the first tester 102A can include any biosignature scan set forth herein, and results in a first biosignature. At t=1, the first biosignature is received at apparatus 110A, and one or more biological tokens 104B, having one or more associated one or more token IDs, are generated based on the biosignature. The generation of the biological tokens 104B can be performed by the processor 102 or by one or more remote processors (e.g., a collection of processors forming a distributed ledger such as a blockchain), optionally based on one or more smart contracts 104J stored locally and/or on the distributed ledger (e.g., a blockchain). Between t=1 and t=3, the biological sample may be transported from the first location to a second location associated with a remote processor. At t=2, the remote processor 114 receives a signal representing one or more of: the token ID, the biological token, and the biosignature (e.g., a biosignature string resulting from the first test). At t=3, the biological sample is again tested (e.g., via a biosignature scan), using a second tester 102B at the second location, to again obtain a second biosignature. The remote processor 114 can then verify the authenticity of the biological sample and/or the biological sample's provenance (i.e., confirming the patient from which the biological sample was derived) by comparing the second biosignature with the first biosignature, or by comparing a hash of the second biosignature with the token ID, to see whether they match or substantially match (e.g., have a similarity higher than a threshold value), as discussed in greater detail below.

Figure 4:
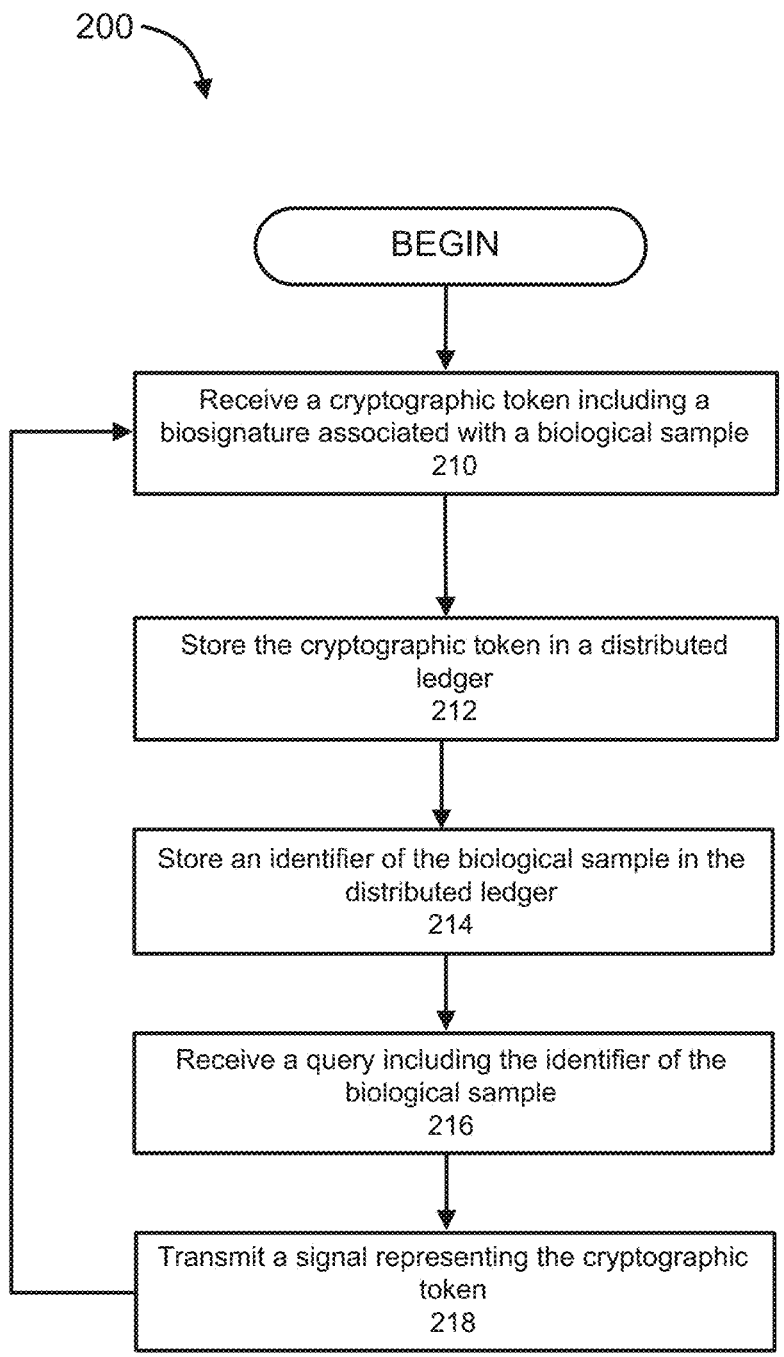
FIG. 4 is a flowchart illustrating a method for validating authenticity of a biological sample, according to some embodiments.

FIG. 4 is a flowchart illustrating a method for validating authenticity of a biological sample, according to some embodiments. As shown in FIG. 4, the method 200 includes receiving, at 210, a cryptographic token (such as a biological token described herein) including a representation of, or generated based on, a biosignature associated with a biological sample. The cryptographic token may be received, for example, at an apparatus such as apparatus 110 of FIG. 1, and/or a remote processor, such as the remote processor 114 of FIG. 1. At 212, the cryptographic token is stored in a distributed ledger, and at 214, an identifier of the biological sample is stored in the distributed ledger. A query is then received, at 216, referencing the identifier of the biological sample. At 218, a signal representing the cryptographic token is transmitted to the sender of the query, as a result of the query.

Generating a Biosignature

Biological samples (also referred to as "biospecimens" or "aliquots") that can be monitored and/or verified using methods and systems of the present disclosure include, but are not limited to, whole blood, blood serum, blood clot, blood plasma, plasma isolate, buffy coat, red blood cells, white blood cells, platelets, lymphocytes, erythrocytes, mononuclear leukocytes, granulocytes, intracellular fluid, extracellular fluid, interstitial fluid, lymph, bile, serum, amniotic fluid, fetal cells, stem cells, synovial fluid, cerebrospinal fluid, breast milk, aqueous humour, metabolic water, pericardial effusion, rheum, colostrum, tumor cells (e.g., circulating tumor cells), reselected tumor sample, fixed tumor slices mounted on slides, extracted deoxyribonucleic acid (DNA), extracted ribonucleic acid (RNA), pus, chyle, chyme, mucus, gastric acid, transudate, urine, feces, hair, nail, tooth, skin, adipose tissue (fat), tears, sweat, buccal cells, earwax, dandruff, saliva, vaginal fluid, semen, sebum, glycocalyx, hemoglobin, musculoskeletal tissue (e.g., bone, cartilage, joint tissue, ligament, tendon, muscle), cheek tissue, placental tissue, organ tissue, pleural fluid, cerebrospinal fluid, or any other biological material having a genetic marker. Biological samples can be prepared, for example, via one or more biological sampling techniques, such as (but not limited to): biopsy (e.g., core biopsy), fine needle aspiration (FNA), excision, pleural fluid aspiration, blood draw, urine collection, phenolchloroform extraction, etc. Biosignatures of the biological samples can be defined through one or a combination of different assays or scans (collectively referred to herein as "biosignature scans"), including (but not limited to), chemical analysis (e.g., analysis of common blood plasma analytes), image-based analysis (e.g., imaging of tumor tissue), DNA analysis, gene sequencing, and biomechanical analysis of suspended tumor cells. In some embodiments, a combination of several parameters (e.g., 10 or fewer parameters) obtained from each assay is used to define the unique biosignature, thereby facilitating the biophysical verification of a patient's biological sample as it moves between locations and/or entities within a supply chain. In some embodiments, a suitable assay for generating the biosignature is an assay that can be completed within a short duration (e.g., 1 minute or less), is reliable (e.g., having a rate of missed readings lower than 5-10%), is inexpensive (e.g., comparable in cost to a simple blood test—~$100-1000, depending on assay used and number of parameters), and/or uses either a minimal amount of the biological sample (e.g., 0.001 mL-0.01 mL of the biological sample) or does not consume any portion of the biological sample at all (e.g., image-based assays). In some embodiments, the type(s) of biosignature scan employed is/are selected based on a tissue type associated with the biological sample. For example, tumor tissue may be tokenized using one or more microscopy techniques, whereas blood plasma may be tokenized using blood plasma analyte analysis. In some embodiments, the biosignature is disease-agnostic. For example, the contents of the biosignature may not include a direct representation, indication, or identifier of a disease and/or may include only representations or indications of parameters, measurements, values, etc. that are independent of any particular disease or that are not, of themselves, sufficient for the identification or diagnosis of a disease. Other token examples include, but are not limited to: tokenization of saliva using a salivary cytokine panel, tokenization of serum using enzyme-linked immunosorbent assay (ELISA) analysis, tokenization of earwax using chromatography and/or mass spectrometry, tokenization of whole blood using a basic metabolic panel, tokenization of placental tissue using chorionic villus sampling, tokenization of amniotic fluid using amniocentesis, and tokenization of urine using one or more of: Benedict's test for glucose, a creatinine colorimetric assay, liquid chromatography-mass spectrometry (LC-MS) analysis, urinometry, or urine osmolality testing. In other words, biosignatures of the present disclosure may be defined, or may include data, such that a disease of a patient cannot be detected or inferred.

Biosignatures described herein can have a data precision sufficient to uniquely identify the biological sample from a plurality of biological samples. Data precision can refer to one or more of: a number of characters within a biosignature string (i.e., a string length of the biosignature), an accuracy of at least a portion/subset of the biosignature, or a reproducibility of at least a portion/subset of the biosignature. Under some circumstances, for example, for a given population of samples being monitored, a biosignature string length of 3 may be insufficient to differentiate or uniquely identify each sample from the population of samples with a certainty above a desired confidence threshold (e.g., 90%), whereas a biosignature string length of 5 may be insufficient to differentiate or uniquely identify each sample from the population of samples with a certainty above the desired confidence threshold. As such, in the foregoing example, the biosignature string with a length of 5 has a data precision sufficient to uniquely identify each biological sample from the population of biological samples.

Generating a Biological Token

In some embodiments, once a biosignature assay or scan has been completed, the results can be concatenated into a biosignature string, for example:

0:1:1:0:1:1:1:0:1:0

The biosignature string, optionally combined with patient identity data and time/date of sample collection, can be stored (e.g., in a memory, such as memory 104 of FIG. 1)

and sent to a smart contract stored in the blockchain, which converts the string into a hash (e.g., using a SHA256 cryptographic hash algorithm) and defines a new non-fungible cryptographic token (the biological token), where the hash becomes the token ID and the additional data is stored as metadata about the biological token, for example as follows:

Token ID: 0xfafd553636eb637c1d295db9f1da3e45927443e3ce0a352b4de3e8bdf628fd0b

Metadata (e.g., stored in a .json key-value pair structure)
"bio-scan": "0:1:1:0:1:1:1:0:1:0"
"Patient Identity Token":
"0xee72022a199d3a8d251cf94b75b9180f717d7d72db74b98e0dd81c1a010957e4"
"Sample Collection Timestamp": "06/14/2018, 2:50 PM EST"
"Sample Collection Location": "Clinic ABC"

Once the biological token has been defined, a physical label for the sample can be generated using the token ID as the unique identifier (e.g., encode via a barcode or stored as an RFID). The biological token or a representation thereof may be generated at the system (e.g., apparatus 110 of FIG. 1) and/or may be received at the system from the blockchain. The biological token data and associated token ID can be locally stored (e.g., in a memory, such as memory 104 of FIG. 1). Accessing the biological token data via the blockchain can subsequently be performed by scanning/reading the token ID of the physical label.

In other embodiments, a biosignature (i.e., based on one or more biosignature assays or scans) for a biological sample is transmitted (e.g., via wireless network communication and/or via a label encoding or containing a representation of the biosignature) to a remote processor without involvement of the blockchain. The remote processor can then verify the authenticity of the biological sample and/or the biological sample's provenance (i.e., confirming the patient from which the biological sample was derived) by performing the same or a similar one or more biosignature assays or scans, and comparing the resulting biosignature with the transmitted biosignature, to see whether they match, or substantially match (e.g., have a similarity higher than a threshold value).

Confirmation/Verification of Biological Samples

In some embodiments, once the token is defined, verification of the biological sample can be performed by:
(1) Accessing the physical sample;
(2) Re-running the biosignature scan; and
(3) (a) Comparing the re-run biosignature scan to the "bio-scan" value (as shown above) in the biological token's metadata, and/or (b) Hashing the raw bio-scan results and comparing the resulting hash to the token ID.

In some embodiments, there will be an appreciable difference between the re-run biosignature and the bio-scan value if the biological sample has been tampered with, for example, during transport and/or storage. An appreciable difference may be defined as a similarity (e.g., between corresponding biosignature string values) of below a predetermined threshold, for example: below about 90%, below about 85%, below about 80%, below about 75% below about 70%, below about 65%, below about 60%, below about 55%, or below about 50% similarity. In some embodiments, verification of the biological sample is performed without using or making reference to a physical packaging (e.g., a box, vial, test tube, container, wrapper, sticker, label, etc.) associated with the biological sample.

Applications of Biological Sample Tokenization

A key application of the methods set forth herein is ensuring accurate identification of a biological material, for example human blood or tissue, or non-human mammalian blood or tissue. As a first example, personalized medical treatment for leukemia patients can include CAR-T treatment(s), involving extraction of the patient's blood, isolation of T-Cells from the patient's blood, design of a patient-specific treatment using those T-Cells, engineering and expansion of the T-Cells (e.g., converting them to CAR-T cells), and infusing the CAR-T into the patient. Throughout this process, there are several transfers, or "hand-offs," of the product (i.e., biological materials such as the blood, T-Cells, CAR-T cells) between participants in the leukemia treatment process. Biosignature-based tokenization methods of the present disclosure can be applied in such applications, to prove chain of custody and preserve provenance information throughout the treatment process, and to ensure that the patient is in fact receiving the proper treatment based on his/her T-Cells. An example implementation includes designing a workflow within a blockchain that governs the CAR-T manufacturing process, and defining one or more biological tokens within that blockchain based on one or more biosignature scans of a relevant biological material. Then, at each intermediate stage in the CAR-T manufacturing process (e.g., after each critical handoff), one or more further biosignature scans can be re-run, to prove/verify that the sample that is being used in the manufacturing process does in fact belong to the patient. The one or more further biosignature scans can be the same as, or similar to, the biosignature scan(s) used to define the one or more biological tokens. Similarly, as a final step, one or more final biosignature scans can be performed prior to infusion of the CAR-T into the patient, to confirm that the individualized treatment does in fact belong to that patient.

As a second example, livestock intended for human consumption can be tokenized based on one or more samples of the livestock's blood, using one or more biosignature scans. The resulting token(s) can then be used to track and monitor the animal throughout its life. Once the meat from the livestock has been processed and distributed within the marketplace, further biosignature scans can be performed (e.g., re-running the same or a similar type of biosignature scan) to generate/replicate the token ID associated with that meat. The replicated token ID can then be used to access the history of that particular product via the blockchain, where it is indelibly stored. As such, systems and methods of the present disclosure can facilitate enhanced monitoring and control of food safety.

As a third example, a biological (e.g., blood, urine, etc.) sample may be taken from a competitive athlete as part of a drug testing program. The biological sample can be characterized using a biosignature scan at the location where the biological sample is collected (e.g., via the same instrument that collected the biological sample or a system in network communication therewith), and "tokenized" such that the biosignature token and its associated token ID can be transmitted to and stored on the blockchain. The biological sample is optionally labelled with a label containing/encoding the token ID, and can then be transported to a geographically disparate testing facility for drug testing. At the testing facility, the biological sample can be reliably verified as belonging to the athlete with which it is presumed to be associated (e.g., per the label or other indication) by re-running the same or similar biosignature scan that was initially performed on the biological sample at the location of collection, and one or both of: comparing the re-run biosignature to metadata of the associated biosignature token on the blockchain, or hashing the re-run biosignature to generate a hash and comparing the hash to the token ID stored on the blockchain.

Tokenized Mapping of Transformative Biological Samples

Some biological samples are "transformative," in that they naturally or spontaneously transform/change (e.g., in structure, disease state, color, size, shape, viscosity, degree of oxidation, etc.) over time, such that biosignature scans performed later in time can differ from an initial biosignature scan performed when the token was defined/generated. Systems set forth herein can capture the transformations described above over time by recording new biosignature tokens to the blockchain at the various points in time. Alternatively, in some embodiments, existing predecessor biosignature tokens may be "consumed" when a new/subsequent biosignature token (associated with a transformed version of the biological sample) is generated. As used herein, the term "consumed" can have a different meaning, depending upon whether the token is a discrete, non-fungible token or a continuous, non-fungible token. Discrete, non-fungible tokens can be tokens associated with materials (such as drugs) that are sold in indivisible units (e.g., as a sealed bottle, a single-use syringe, a transdermal patch, etc.). Discrete, non-fungible tokens are relatively easy to count in their base unit (typically an EACH) and can be used in their entirety. Consuming a discrete, non-fungible token can include sending the discrete, non-fungible token to a "burn location" (e.g., a blockchain address that, for example, has no associated private key) such that the discrete, non-fungible token cannot be moved out/retrieved. By contrast, continuous, non-fungible tokens can be tokens associated with materials (such as drugs, raw materials, etc.) for which the lowest saleable unit is non-fungible (i.e., a specific batch or lot) but can be used in fractions that are not typically known/determined in advance. For example, a 1 mL vial could be used for two 0.5 mL injections or four 0.25 mL injections. Continuous, non-fungible tokens can include an additional, dynamic attribute (i.e., a "quantity" attribute) that can be decremented. Consuming a continuous, non-fungible token can refer to using only a portion/subset of the continuous, non-fungible token (e.g., as the quantity attribute is dynamically decremented). Once the quantity attribute reaches a value of zero, the continuous, non-fungible token can be sent to the burn location referenced above (in relation to the continuous, non-fungible token).

For example, in a gene therapy context, the original blood sample can have a biosignature (which may be tokenized as a "blood token") that is based on blood. The blood sample is taken to a sequencing center where the sample is used to obtain an associated genomic sequence (which can also, optionally, be tokenized as a "genome token"). During the process of "creating" the genome token, all or a portion of the blood token will be consumed via a single or related series of transactions on the blockchain. The consumption of the blood token via the genome token creation process creates a permanent linkage between the tokens. In the event of full consumption, this effectively "transforms" the bio-sample token into a genome token. Similarly, if the genome token is used to create a custom treatment, a treatment token for the custom treatment can reference the genome token (optionally without destruction of the genome token).

In some embodiments, an authenticity of a biological sample can be determined, at least in part, by evaluating one or more historical biosignature tokens and/or associated stored data to determine whether a combination of the data thereof (e.g., biosignature, date of biosignature, time of biosignature, location of biosignature, metadata, patient information, environmental data during shipping and/or storage (e.g., temperature, humidity, and/or light conditions), transport data (e.g., via air or ground) or any combination thereof) could logically and/or logistically have coexisted. Such an evaluation could also take into account a current date, time, location, and/or sample condition at the time of the evaluation. If properties/conditions represented by the data could not have logically and/or logistically coexisted (e.g., the sample could not have been 1,000 miles away 30 minutes ago, or urine collected one week ago should show signs of oxidation but currently does not), the sample can be deemed to be corrupt or inauthentic. A system to perform such evaluations can include a processor and a memory operably coupled to the processor and storing instructions to cause the processor to compare the foregoing data, detect a mismatch (e.g., according to a set of rules, a table, and/or one or more algorithms), store an association between an identifier of the biological sample and the mismatch, and optionally send a signal to cause display (e.g., via a graphical user interface (GUI)) of an alert message to a user of the system. In some implementations, data associated with the mismatch can be recorded to a distributed ledger. The mismatch can represent one or more of: an inconsistency, incompatibility, disparity, or impermissible variance (e.g., a variance value outside a predefined range of expected values). As an example, a urine sample stored and/or transported at room temperature for longer than 24 hours can be expected to exhibit one or more or the following biochemical and/or microbiological changes: increased pH and alkalinity due to the breakdown of urea and ammonia, darkened color due to oxidation or reduction of metabolites, increased turbidity due to bacterial growth and crystal precipitation, foul odor due to bacterial decomposition of urea and ammonia, reduced or eliminated presence of casts due to their dissolution, decreased glucose due to glycolysis, decreased bilirubin and/or color change of bilirubin from yellow to green due to oxidation to biliverdin, decreased urobilinogen and/or color change of urobilinogen from colorless to orange-red due to oxidation to urobilin, decreased acetone/ketones due to evaporation, decreased acetoacetic acid due to its conversion into acetone, increased nitrite due to bacterial production, decrease or elimination of cells due to lysis, lysis of red blood cells due to urine alkalinity, disintegration of white blood cells due to dilute urine alkalinity, and increased bacteria count due to bacterial proliferation.

Biological Sample Differentiation within a Lot of Biological Samples

In some embodiments, a biological sample may be one of a finite lot of multiple biological samples, where a number of biological samples in the lot is of a moderate size (e.g., 10, 25, 50, 100, 500, 1,000, or 10,000 samples). A biosignature may be generated (via a biosignature scan) for each biological sample from the lot prior to shipment of the lot to a remote processing facility. The biosignatures (or a subset thereof) can be sent to a smart contract of a distributed ledger (e.g., blockchain) for conversion into associated biological tokens (each including a hash (or token ID) of a biosignature and metadata, as discussed above). Optionally, a label encoding or containing the token ID is applied or affixed to each biological sample (or a subset thereof) or a packaging associated with each biological sample (or a subset thereof). One or both of the biosignatures and the token IDs can be sent to a remote processor at the remote processing facility. Once the lot of biological samples arrives at the remote processing facility, one or more of the biological samples from the lot can be verified to be authentic and/or associated with a given patient, by re-running the biosignature scan (thereby generating raw bio-scan results) and comparing the re-run biosignature scan to the "bio-scan" value in the biological token metadata. In some embodiments, re-running the biosignature scan facilitates the verification of a biological sample via differentiation or distinguishing of that one biological sample from the lot of biological samples, e.g., with absolute certainty, or with a predetermined degree of certainty. For applications where the objective is to verify a biological sample via differentiation from other biological samples in a lot, the biosignature scan can include a technique having a time-to-completion that is less than a time-to-completion of DNA sequencing for the sample biological sample. For example, the time to perform the biosignature scan can be on the order of minutes (e.g., less than about 1 minute, between about 1 minute and about 10 minutes, or between about 5 minutes and about 30 minutes, or less than about an hour), whereas the time to complete DNA sequencing can be on the order of days. In other words, for applications in which a biological sample is being differentiated from, or identified from among, biological samples of a finite lot or relatively small or moderate size, a lower resolution of the biological sample characterization technique may be sufficient to achieve the desirable degree of accuracy.

In some embodiments, a system includes a plurality of apparatuses, each apparatus from the plurality of apparatuses including a tester, a processor, and a memory operably coupled to the processor. The tester is configured to detect, within a predetermined test duration, a biological signature of a biological sample of a lot of biological samples, the lot of biological samples including a predetermined number of biological samples. The memory stores instructions to cause the processor to generate a cryptographic token including a digital identifier based on the biological signature, and to transmit the cryptographic token to a remote processor configured to verify the biological sample in response to receiving the cryptographic token.

In some embodiments, for each apparatus from the plurality of apparatuses, the memory stores instructions to cause the processor to generate the cryptographic token using a smart contract and through communication with a distributed ledger. For each apparatus from the plurality of apparatuses, the tester can be configured to perform a first test on the biological sample to detect the biological signature, and the cryptographic token is transmitted to the remote processor such that the remote processor verifies the biological sample by performing a second test on the biological sample, the second test being substantially the same as the first test.

In some embodiments, for each apparatus from the plurality of apparatuses, the tester is configured to perform a first test on the biological sample to detect the biological signature, and the cryptographic token is transmitted to the remote processor such that the remote processor verifies the biological sample. The verification can be based on: (1) performing a second test on the biological sample, the second test being substantially the same as the first test and comparing the first test to the second test; and (2) at least one of a label or a radio frequency identification (RFID) tag or chip associated with the biological sample.

In some embodiments, for each apparatus from the plurality of apparatuses, the predetermined test duration is less than about one minute, or less than about five minutes, or less than about ten minutes, or less than about 15 minutes, or less than about 20 minutes, or less than about 30 minutes, or less than about 45 minutes, or less than about one hour.

For each apparatus from the plurality of apparatuses, the biological sample can include at least one of: whole blood, plasma isolate, circulating tumor cells, a reselected tumor portion, and a fixed tumor slice.

In some embodiments, a method includes receiving a signal representing a first cryptographic token including a biosignature associated with a biological sample, and storing, in response to receiving the signal, a representation of the first cryptographic token and an identifier of the biological sample in a distributed ledger. A query is received, the query including the identifier of the biological sample, and in response to and based on the query, a signal representing the cryptographic token is transmitted. The biosignature (e.g., blood plasma analyte analysis biosignature, an image-based analysis biosignature, or a biomechanical analysis biosignature) can be generated using a test methodology, and each of the first sample verification and the second sample verification can be performed using the test methodology. The query can be a first query, received from a server associated with an intermediate testing facility. The intermediate testing facility can be, for example, a physical location such as a building (e.g., a hospital), an aircraft, or a vehicle (e.g., an ambulance), optionally located between a source location where the biosignature was originally generated (i.e., a location where a first tester resides) and a destination facility (e.g., a physical location such as a building or a hospital) to which the biological sample may be transported. The original biosignature may be generated by the first tester (such as tester 102A in FIG. 3), the intermediate testing facility can include a second tester configured to perform the test methodology, and the destination facility can include a third tester (such as tester 102B in FIG. 3). The transmitting the signal representing the cryptographic token can be to the server associated with an intermediate testing facility for a first sample verification. The method can also include receiving, from a server associated with a destination facility, a second query including the identifier of the biological sample, and transmitting, in response to and based on the second query, a signal representing the cryptographic token to the server associated with the destination facility for a second sample verification. In some embodiments, the method also includes storing chain-of-custody information including data associated with the first sample verification and data associated with the second sample verification.

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

To address various issues and advance the art, the entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. They are presented to assist in understanding and teach the embodiments.

It should be understood that they are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisional s, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure.

The invention claimed is:

1. An apparatus, comprising:
a processor; and
a memory operably coupled to the processor and storing instructions to cause the processor to:
receive an indication of a biological signature from a tester, the biological signature associated with a biological sample and having a data precision sufficient to uniquely identify the biological sample from a plurality of biological samples, the tester configured to detect the biological signature within a predetermined test duration that is less than a DNA sequencing duration associated with the biological sample;
initiate generation, using a smart contract and through communication with a distributed ledger, of a cryptographic token including (1) a digital identifier based on the biological signature, and (2) a representation of at least one of a date, a time, a location, or patient information, and
transmit the cryptographic token to a remote processor configured to verify the biological sample in response to receiving the cryptographic token.

2. The apparatus of claim 1, wherein the memory further stores instructions to cause the processor to transmit the cryptographic token for storage on the distributed ledger.

3. The apparatus of claim 1, wherein the memory further stores instructions to cause the processor to transmit the cryptographic token for storage, as a blockchain transaction record, in the distributed ledger, and
the cryptographic token is transmitted to the remote processor such that the remote processor verifies the biological sample by including retrieval of the blockchain transaction record.

4. The apparatus of claim 1, wherein the biological signature is a disease-agnostic biological signature.

5. The apparatus of claim 1, wherein the biological sample includes one of blood, urine, saliva, hair, musculoskeletal tissue, or nail.

6. The apparatus of claim 1, wherein the biological sample includes tumor tissue, and the tester is configured to detect the biological signature of the biological sample using image-based analysis.

7. A system, comprising:
a plurality of apparatuses, each apparatus from the plurality of apparatuses including:
a processor; and
a memory operably coupled to the processor and storing instructions to cause the processor to:
receive, from a tester, a biological signature of a biological sample from a lot of biological samples, the biological signature having a data precision sufficient to uniquely identify the biological sample from a plurality of biological samples, the tester configured to detect the biological signature within a predetermined test duration that is less than a DNA sequencing duration associated with the biological sample;
generate a cryptographic token including (1) a digital identifier based on the biological signature, and (2) a representation of at least one of a date, a time, a location, or patient information, and
transmit the cryptographic token to a remote processor configured to verify the biological sample in response to receiving the cryptographic token.

8. The system of claim 7, wherein, for each apparatus from the plurality of apparatuses, the memory stores instructions to cause the processor to generate the cryptographic token using a smart contract and through communication with a distributed ledger.

9. The system of claim 7, wherein, for each apparatus from the plurality of apparatuses:
the tester is configured to perform a first test on the biological sample to detect the biological signature, and
the cryptographic token is transmitted to the remote processor such that the remote processor verifies the biological sample by performing a second test on the biological sample, the second test being substantially the same as the first test.

10. The system of claim 7, wherein, for each apparatus from the plurality of apparatuses:
the tester is configured to perform a first test on the biological sample to detect the biological signature, and
the cryptographic token is transmitted to the remote processor such that the remote processor verifies the biological sample based on: (1) performing a second test on the biological sample, the second test being substantially the same as the first test, and comparing results of the first test to results of the second test; and (2) at least one of a label or a radio frequency identification (RFID) tag associated with the biological sample.

11. The system of claim 7, wherein, for each apparatus from the plurality of apparatuses, the cryptographic token is transmitted to the remote processor such that the remote processor verifies the biological sample without using a packaging associated with the biological sample.

12. The system of claim 7, wherein, for each apparatus from the plurality of apparatuses, the predetermined test duration is less than about one minute.

13. The system of claim 7, wherein, for each apparatus from the plurality of apparatuses, the biological sample includes at least one of: whole blood, plasma isolate, circulating tumor cells, urine, saliva, hair, musculoskeletal tissue, nail, a resected tumor portion, and a fixed tumor slice.

14. A method, comprising:
receiving a signal representing a cryptographic token including (1) a representation of a biosignature that is associated with a biological sample and that was detected by a tester within a predetermined test duration that is less than a DNA sequencing duration associated with the biological sample, and (2) a representation of at least one of a date, a time, a location, or patient information, the biosignature having a data precision sufficient to uniquely identify the biological sample from a plurality of biological samples;
storing, in response to receiving the signal, a representation of the cryptographic token in a distributed ledger;
storing, in response to receiving the signal, an identifier of the biological sample in the distributed ledger; and
after storing the representation of the cryptographic token and the identifier of the biological sample:
receiving a query including the identifier of the biological sample; and
transmitting, in response to and based on the query, a signal representing the cryptographic token.

15. The method of claim 14, wherein the query is a first query and the cryptographic token is a first cryptographic token, the first query received from a server associated with an intermediate testing facility, the transmitting the signal representing the cryptographic token being to the server associated with an intermediate testing facility for a first sample verification, the method further comprising:
receiving, from a server associated with a destination facility, a second query including the identifier of the biological sample; and
transmitting, in response to and based on the second query, a signal representing the cryptographic token to the server associated with the destination facility for a second sample verification.

16. The method of claim 15, further comprising storing chain-of-custody information including data associated with the first sample verification and data associated with the second sample verification.

17. The method of claim 14, wherein the biosignature is generated using a test methodology, and each of the first sample verification and the second sample verification is performed using the test methodology.

18. The method of claim 14, wherein the biosignature is a blood plasma analyte analysis biosignature, an image-based analysis biosignature, or a biomechanical analysis biosignature.

* * * * *

UNITED STATES PATENT AND TRADEMARK OFFICE
CERTIFICATE OF CORRECTION

PATENT NO. : 11,206,138 B2
APPLICATION NO. : 16/654720
DATED : December 21, 2021
INVENTOR(S) : James C. Canterbury et al.

It is certified that error appears in the above-identified patent and that said Letters Patent is hereby corrected as shown below:

In the Specification

Column 5, Line 45: "reselected" should read --resected--.
Column 12, Line 3: "reselected" should read --resected--.
Column 13, Line 56: "divisional 3" should read --divisionals--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*